United States Patent
Rahman

(10) Patent No.: US 7,314,637 B1
(45) Date of Patent: *Jan. 1, 2008

(54) METHOD OF ADMINISTERING LIPOSOMAL ENCAPSULATED TAXANE

(75) Inventor: Aquilar Rahman, Long Grove, IL (US)

(73) Assignee: Neopharm, Inc., Lake Forest, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/239,598

(22) PCT Filed: Jun. 29, 1999

(86) PCT No.: PCT/US99/14986

§ 371 (c)(1),
(2), (4) Date: Feb. 25, 2000

(87) PCT Pub. No.: WO00/01366

PCT Pub. Date: Jan. 13, 2000

(51) Int. Cl.
*A61K 9/127* (2006.01)
(52) U.S. Cl. .................. 424/450; 514/449; 514/510
(58) Field of Classification Search .......... 424/450; 514/449, 510
See application file for complete search history.

(56) References Cited

U.S. PATENT DOCUMENTS

| | | |
|---|---|---|
| 4,534,899 A | 8/1985 | Sears |
| 4,861,580 A | 8/1989 | Janoff et al. |
| 4,898,735 A | 2/1990 | Barenholz et al. |
| 4,927,571 A | 5/1990 | Huang et al. |
| 4,952,408 A | 8/1990 | Rahman |
| 4,960,790 A | 10/1990 | Stella et al. |
| 5,041,278 A | 8/1991 | Janoff et al. |
| 5,059,591 A | 10/1991 | Janoff et al. |
| 5,094,854 A | 3/1992 | Ogawa et al. |
| 5,234,634 A | 8/1993 | Janoff et al. |
| 5,330,689 A | 7/1994 | Janoff et al. |
| 5,415,869 A | 5/1995 | Straubinger et al. |
| 5,424,073 A * | 6/1995 | Rahman et al. ............ 424/450 |
| 5,534,499 A | 7/1996 | Ansell |
| 5,554,382 A | 9/1996 | Castor |
| 5,565,478 A | 10/1996 | Kohn et al. |
| 5,621,001 A | 4/1997 | Canetta et al. |
| 5,641,803 A | 6/1997 | Carretta et al. |
| 5,648,090 A | 7/1997 | Rahman et al. |
| 5,665,761 A | 9/1997 | Canetta et al. |
| 5,670,537 A | 9/1997 | Canetta et al. |
| 5,683,715 A * | 11/1997 | Boni et al. ............... 424/450 |
| 5,696,153 A | 12/1997 | Ainsworth et al. |
| 5,756,537 A * | 5/1998 | Gill ............................ 514/449 |
| 5,919,816 A | 7/1999 | Hausheer et al. |
| 5,994,409 A | 11/1999 | Stogniew et al. |
| 6,066,331 A | 5/2000 | Barenholz et al. |
| 6,090,955 A | 7/2000 | Reszka et al. |
| 6,118,011 A | 9/2000 | Mayhew et al. |
| 6,146,659 A * | 11/2000 | Rahman ................... 424/450 |
| 6,461,637 B1 * | 10/2002 | Rahman ................... 424/450 |

FOREIGN PATENT DOCUMENTS

| | | |
|---|---|---|
| CA | 2132711 A1 | 9/1993 |
| CA | 2153326 A1 | 5/1995 |
| CA | 2294981 A1 | 1/1999 |
| EP | 0750910 A1 | 1/1997 |
| EP | 0776202 B1 | 5/2000 |
| HU | 217839 B | 1/1993 |
| HU | P9903952 A | 9/1997 |
| JP | 2-503558 A | 10/1990 |
| JP | 6-329533 A | 11/1994 |
| JP | 8-034745 A | 2/1996 |
| JP | 8-508046 A | 8/1996 |
| JP | 9-315978 A | 12/1997 |
| WO | WO 82/03769 A1 | 11/1982 |
| WO | WO 88/09168 A1 | 12/1988 |
| WO | WO 93/18751 A1 | 9/1993 |
| WO | WO 95/13053 A1 | 5/1995 |
| WO | WO 96/15774 A1 | 5/1996 |
| WO | WO 96/21658 A1 | 7/1996 |
| WO | WO 97/10234 A1 | 3/1997 |
| WO | WO 00/01366 A1 | 1/2000 |

OTHER PUBLICATIONS

Pharmaceutical Research, vol. 11, No. 2, 1994, pp. 206-212, XP000874375 "A Mixed Micellar Formulation Suitable for the Parenteral Administration of Taxol".

Agata et al., "Anti-Tumor Activity of Docetaxel in Non-small Cell Lung Cancer Xenografts is Potentiated by NM-3, an Angiogenesis Inhibitor," *ILEX Products, Inc.*, Abstract No. 2752.

Ali et al., "Hyrolyzable Hydrophobic Taxanes: Synthesis and Anti-Cancer Activities," *Anti-Cancer Drugs*, 12, 117-128 (2001).

(Continued)

Primary Examiner—Gollamudi S. Ksihore

(57) ABSTRACT

Liposomal-encapsulated taxane or an antineoplastic derivative thereof or a mixture thereof is provided which is used to effect a therapeutically enhanced method of treating cancer. The liposomal encapsulated paclitaxel allows for administration to a patient, particularly a human patient, in less than one hour without substantial toxicity.

42 Claims, No Drawings

OTHER PUBLICATIONS

Essayan et al., "Successful Parenteral Desensitization to Paclitaxel," *J. Allergy Clin. Immunol.*, 97(1), 42-46 (1996).

Gelderblom et al., "Influence of Cremophor EL on the Bioavailability of Intraperitoneal Paclitaxel," *Clinical Cancer Research*, 8, 1237-1241 (2002).

Henningsson et al., "Mechanism-Based Pharmacokinetic Model for Paclitaxel," *J. of Clinical Oncology*, 19(20), 4065-4073 (2001).

Holton et al., "Oral Anti-Tumor Activity of TL00139 (MAC-321) A New Taxane," *Annual Meeting of the American Association for Cancer Research*, Abstact No. 2732, (2003).

Longley et al., "In Vitro Mechanism of Action Studies With the Taxane Analog—TL00139 (MAC-321)," *Annual Meeting of the American Association for Cancer Research*, Abstact No. 2733, (2003).

Marty et al., "A Comparison of Docetaxel and Paclitaxel Against Adult Human Solid Tumor Xenografts in Nude Mice," *IDD*, Abstract No. 2757 (2003).

Southwell et al., "Antitumor Activity of Taxotere and Paclitaxel Against Three Human Pediatric Tumor Xenograft Models," *IDD*, Abstract No. 2759 (2003).

Sparreboom et al., "Preclinical Pharmacokinetics of Paclitaxel and Docetaxel," *Anti-Cancer Drug*, 9, 1-17 (1998).

Sparreboom et al., "Tissue Distribution, Metabolism and Excretion of Paclitaxel in Mice," *Anti-Cancer Drugs*, 7, 78-86 (1996).

Sparreboom et al., "Introduction: Recent Topics in the Clinical Pharmacology of Taxanes that Might Change Future Perspectives," *Investigational New Drugs*, 19, 111-112 (2001).

Sparreboom et al., "Cremophor EL-mediated Alteration of Paclitaxel Distribution in Human Blood: Clinical Pharmacokinetic Implications," *Cancer Research*, 59, 1454-1457 (1999).

Zuylen et al., "Role of Formulation Vehicles in Taxane Pharmacology," *Investigational New Drugs*, 19, 125-141 (2001).

Bonadonna, Annals of Oncology, 3, 417-418 (1992).

Devries, Annals of Oncology, 3, 419-421 (1992).

Hoeprich, "Clinical Use of Amphotericin B and Derivatives: Lore, Mystique and Fact," *Clinical Infectious Disease*, 14(Suppl 1), S114-S119 (1992).

Johnson, "Taxol," *Physicians' Desk Reference*, PDR 54th Eds., 881-887 (2000).

"Liposomes" Ed. By Ostro, Marcel Dekker, Inc., Chp. 9, 227-338 (1987).

Petit et al., "In-vivo therapeutic efficacy in experimental murine mycoses of a new formulation of deoxycholate-amphotericin B obtained by mild heating," *J. of Antimicrobial Chemotherapy*, 42, 779-785 (1998).

Romanellie et al., "In vitro and in vivo interaction between cisplatin and topotecan in ovarian carcinoma systems," *Cancer Chemother Pharmacol.*, 41, 385-390 (1998).

Riondel et al., In Vivo, 6, 23-27 (1992).

Rahman et al., Cancer Research, 42, 1817-1825 (1982).

Rahman et al., Cancer Chemother. Pharmacol., 16, 22-27 (1986).

Rahman et al., Chemical Abstracts, Abstract No. 104(102092), (Mar. 31, 1986).

Ostro, American Journal Hosp. Pharm., 46, 1576-1587 (1989).

Rosa, Transplant Biochem. Model Syn. Res., 243-256 (1982).

Brown et al., "A phase I trial of Taxol given by a 6-hour intravenous infusion," *J. Clin. Oncol.*, 9 (7), 1261-1267 (Jul. 1991).

Donehower et al., "Phase I trial of Taxol in patients with advanced cancer," *Cancer Treat. Rep.*, 71 (12), 1171-1177 (Dec. 1987).

Eisenhauer et al., "European-Canadian randomized trial of paclitaxel in relapsed ovarian cancer: High-dose versus low-dose and long versus short infusion," *J. Clin. Oncol.*, 12 (12), 2654-2666 (Dec. 1994).

Gianni et al., "Nonlinear pharmacokinetics and metabolism of paclitaxel and its pharmacokinetic/pharmacodynamic relationships in humans," *J. Clin. Oncol.*, 13 (1), 180-190 (Jan. 1995).

Huizing et al., "Pharmacokinetics of paclitaxel and metabolites in a randomized comparative study in platinum-pretreated ovarian cancer patients," *J. Clin. Oncol.*, 11 (11), 2127-2135 (Nov. 1993).

Onyuksel et al., *Pharmaceutical Research*, 11(2), 206-212 (1994).

U.S. Appl. No. 10/266,030, filed Oct. 7, 2002, Rahmen.

McGuire et al., "Taxol: A unique antineoplastic agent with significant activity in advanced ovarian epithelial neoplasms," *Ann. Intern. Med.*, III (4), 273-279 (Aug. 15, 1989).

Saville et al., "Phase II study of paclitaxel (Taxol™) for the treatment of HIV-associated Kaposi's sarcoma (KS)," *Blood*, 84 (10, Suppl. 1), 248a (Abstract 977) (Nov. 15, 1994).

Saville et al., "Treatment of HIV-associated Kaposi's sarcoma with paclitaxel," *The Lancet*, 346, 26-28 (Jul. 1, 1995).

Straubinger et al., "Novel Taxol formulations: Taxol-containing liposomes," *Monogr. Natl. Cancer Inst.*, 15, 69-78 (1993).

Wiernik et al., "Phase I trial of Taxol given as a 24-hour infusion every 21 days: Responses observed in metastatic melanoma," *J. Clin. Oncol.*, 5 (8), 1232-1239 (Aug. 1987).

\* cited by examiner

METHOD OF ADMINISTERING LIPOSOMAL ENCAPSULATED TAXANE

TECHNICAL FIELD OF THE INVENTION

The present invention relates to a method of administering a liposomal encapsulated taxane.

BACKGROUND OF THE INVENTION

The use of taxanes, such as paclitaxel, as anti-tumor agents for patients suffering from diseases such as ovarian and breast cancer, is known. In addition, paclitaxel has been shown to be clinically potent as a synergistic agent when used in conjunction with radiation treatment. Paclitaxel has a unique mechanism of action and a broad spectrum of anticancer activity because paclitaxel shows stabilization of microtubules rather than disassembly of microtubules.

However, paclitaxel has extremely low solubility in water, which makes it difficult to provide a suitable dosage form. Currently, paclitaxel is prepared and administered in a vehicle containing Cremophor EL (a polyethoxylated castor oil) and ethanol in a 50:50 (vol/vol) ratio. This solution is diluted 1:10 in saline before being administered to humans. The stability of paclitaxel once diluted in saline solution is quite low. The drug degrades within 24 hours and, thus, handling of dosage for the patients becomes very difficult. Since, the drug precipitates from dilution, an on-line filter is utilized for the infusion of the drug to the patients.

In clinical trials, a consistent problem of anaphylactoid reaction, dyspnea, hypertension, and flushing have been encountered. The dose-limiting toxicity is myelosuppression which necessitates patient hospitalization when the drug is used.

Attempts to prevent paclitaxel cardiotoxicity and anaphylactoid reaction have included reliance on pretreatment of patients with antihistamine and corticosteroids, and by prolonging the infusion time from six to twenty four hours. U.S. Pat. No. 5,621,001 (Canetta et al.) discloses a prolonged infusion time in a method for reducing peripheral neurotoxicity symptoms while maintaining an anti-tumor effect in patients suffering from ovarian cancer and undergoing paclitaxel therapy. This method involves administering about 135 mg/m$^2$ of paclitaxel over a period of about 24 hours. The administration of paclitaxel is repeated at least once, about 21 days after the preceding administration.

U.S. Pat. No. 5,665,761 (Canetta et al.) discloses a pretreatment stage before administration of paclitaxel. The '761 patent provides for paclitaxel infusions over a duration of less than six hours, preferably about three hours, utilizing dosages of between about 135 mg/m$^2$ and about 275 mg/m$^2$, preferably between about 135 mg/m$^2$ and about 175 mg/m$^2$, after patients had been pretreated to alleviate or minimize hypersensitivity responses. For example, the patients are pre-medicated with steroids, antihistamines, and H$_2$-antagonists sufficient to at least prevent an anaphylactoid shock capable of causing acute hypersensitivity reactions and patient death. U.S. Pat. No. 5,670,537 (Canetta et al.) also discloses this method of administration for a patient suffering from a paclitaxel-sensitive tumor, such as an ovarian tumor.

U.S. Pat. No. 5,641,803, discloses the administration of paclitaxel to a patient, wherein about 135-175 mg/m$^2$ of paclitaxel is administered over a period of about three hours. Such a period purportedly was used to overcome, in part, some of the aforementioned problems associated with short infusion times, such as one hour, which had been employed with the conventional paclitaxel formulations containing polyethoxylated castor oil.

In yet another attempt to address the toxicity concerns of the conventional paclitaxel formulation, U.S. Pat. No. 5,696,153 suggests the use of an administration regimen wherein 45 to 120 mg/m$^2$ of paclitaxel is administered over a period of 60 to 180 minutes, a plurality of times during a 21 day period, with each infusion being separated by an interval of between 4 to 5 days.

However, even with these manipulations of prolonged infusion time and pretreatment of patients with antihistamines and corticosteroids, the patients suffer from serious toxicities which are often fatal. Different agent delivery systems are being utilized to enhance tumor cell-fighting effects of the drug and/or reduce systemic toxicity. Liposomes are one of many carriers that have been developed to help anti-tumor agents become more efficient and less toxic. A "liposome" is a closed structure composed of lipid bilayers surrounding an internal aqueous space.

U.S. Pat. No. 5,648,090 (Rahman et al.) and U.S. Pat. No. 5,424,073 (Rahman et al.) provide a liposomal encapsulated paclitaxel for a method for treating cancer in mammals using such a liposomal-encapsulated paclitaxel, or antineoplastic derivative thereof. The '090 and '073 patents disclose a method of modulating multidrug resistance in cancer cells in a mammalian host by administering to the host a pharmaceutical composition of a therapeutically effective number of liposomes which include a liposome-forming material, cardiolipin, and an agent such as paclitaxel, or an antineoplastic derivative of paclitaxel, or a mixture thereof; and a pharmaceutically acceptable excipient.

Up until the present invention the fastest administration time tolerated by most patients was optimally a three hour time period. Consequently, there is a need for methods for rapidly administering high concentrations of taxane in human cancer patients without inducing a toxic reaction. Such methods would improve the efficacy of taxane therapy and alleviate the discomfort and toxicity associated with previously known taxane administration methods. The present invention provides such a method.

SUMMARY OF THE INVENTION

The present invention provides a method of administering relatively high concentrations of taxane to human patients over a short period of time. For example, taxane can be administered to humans in less than an hour in an amount from about 75 to 300 mg/m$^2$. Unique liposomal formulations of taxane or its antineoplastic derivatives facilitate such treatments. The method does not require premedication, as with anti-hypersensitivity agents, and is not accompanied by substantial toxic reactions in human patients. As a result, the present invention provides an improved method for treating cancer with taxane.

These and other advantages of the present invention, as well as additional inventive features, will be apparent from the description of the invention provided herein.

The invention may best be understood with reference to the following detailed description of the preferred embodiments.

DESCRIPTION OF THE PREFERRED EMBODIMENTS

The present invention provides a method of administering a taxane to a patient, especially a human patient, in need of treatment with a taxane. In part, the present invention provides a delivery system for a taxane to a host which is characterized by the avoidance of solubility problems of a taxane; the improved taxane stability; the avoidance of anaphylactoid reactions and cardiotoxicity; the ability to administer a taxane as a bolus or short infusion, rather than an extended infusion of free taxane; the increased therapeutic efficacy of taxane; and the modulation of multidrug resistance in cancer cells.

The taxane is delivered in the form of a liposomal encapsulated taxane or antineoplastic derivative thereof. Any suitable taxane or derivative can be used in the present method. Suitable taxanes when used in accordance with the disclosed methods provide the aforementioned benefits. Preferably, the taxane is paclitaxel. A suitable derivative of paclitaxel is taxasm. Other suitable taxanes are 7-epipaclitaxel, t-acetyl paclitaxel, 10-desacetyl-paclitaxel, 10-desacetyl-7-epipaclitaxel, 7-xylosylpaclitaxel, 10-desacetyl-7-glutarylpaclitaxel, 7-N,N-dimethylglycylpaclitaxel, 7-L-alanylpaclitaxel, taxotere, and mixtures thereof.

The pharmaceutical composition may also include a suitable cardiolipin. Suitable cardiolipin may be from either a natural or synthetic source. The taxane, such as paclitaxel, is encapsulated in liposomes using the cardiolipin. In addition to cardiolipin, the taxane may be encapsulated in liposomes with phosphatidylcholine and cholesterol. Such lipid compositions provide over 90% encapsulation of the drug in liposomes.

The liposomal encapsulated taxane can be prepared by any suitable process. For example, the taxane or a derivative thereof can be dissolved in a suitable solvent. Generally, suitable solvents are non-polar or slightly polar and can be evaporated without leaving toxic residue behind. Suitable solvents include such diverse solvents as ethanol, methanol, chloroform, butanol or acetone. Cardiolipin can also be dissolved in a suitable solvent as described for taxane and the taxane and the cardiolipin solutions can be mixed. The remaining lipophilic material can be dissolved in a suitable solvent, which may be the same as or different from the taxane containing solvent. The solvent will have low polarity such as chloroform, butanol or a non-polar solvent, such as n-hexane. The solvent mixture containing the taxane and cardiolipin can be mixed with the solution containing the remaining lipophilic components.

The solvent is removed, from the mixture by a suitable method such as by lyophilization to afford a dry lipid film that contains the drug. The mixture is stored in this form, optionally under an inert gas atmosphere, such as an $N_2$ atmosphere. The dry lipid film can be stored at low temperatures, such as −20° C. for extended periods of time until liposomes are hydrated and prior to use.

Liposomes can be formed by adding any suitable solution to the lipid film. Typically, suitable solutions are polar solutions, preferably, aqueous saline solutions. Once the solution is added, liposomes can be formed by mixing, for example, as by vortexing. Where smaller vesicles, such as unilamellar vesicles, are desirable the solution can be sonicated. In certain methods, suitable preparations can be mixtures of multilamellar vesicles and unilamellar vesicles.

The liposome is a closed structure composed of lipid bilayers surrounding an internal aqueous space. Generally, the liposomes may be neutral, negative or positively charged liposomes. For example, positively charged liposomes can be formed from a solution containing phosphatidyl choline, cholesterol, and stearyl amine. Negative liposomes can be formed, for example, from solutions containing phosphatidyl choline, cholesterol, and phosphatidyl serine or more preferably, cardiolipin. Other additives can also be included in the liposomes to modify the properties of the resulting preparations. For example, preferred preparations also include α-tocopherol.

Storage conditions can vary. Preferably, mixtures of lipophilic components are stored as dry lipid films at about −20° C. Once hydrated, liposome suspensions of the pharmaceutical composition can be stored and are stable in buffered, neutral pH saline solutions for periods of hours to months, depending upon the temperature, paclitaxel content, and phospholipid constituents.

The liposomal drug delivery system which features a high drug to carrier ratio can alter drug pharmacokinetics, maintaining the plasma concentration of the drug at an increased level over a longer period of time. The biodegradability and the low inherent toxicity and immunogenicity of liposomal preparations reduces toxicity with respect to free-floating taxanes in the plasma.

The present liposomal formulations provide a drug-delivery system which allows infusion of high concentrations of taxane in a relatively stable form and which provides sustained therapeutic benefits at target sites, while maintaining low concentrations of insoluble free taxane and minimal adverse toxic effects than were previously known. For example, infusion of encapsulated paclitaxel provides higher peak plasma concentrations, longer presence of the drug in the body, and higher AUC ("area under the curve" measurement of plasma concentration over time) than the conventional paclitaxel.

The present pharmaceutical composition can be administered in amounts of at least 50 to 300 mg of active compound/$m^2$ of mammalian host surface area, within a period of less than about three hours, preferably in less than about one hour, and most preferably 45 minutes without causing a substantial toxic reaction. For example, in a 70 kg human, about 0.5 to 5.0 mg active compound per kg of body weight can be safely administered in about 45 minutes. Preferably, about 1.0-3.0 mg of active compound per kg of body weight is administered. Alternatively, preferable amounts include 75, 135, 175, 250, and 300 mg/$m^2$.

Liposomal encapsulated taxane has a substantial beneficial effect in overcoming multidrug resistance in cancer cells which are subjected to chemotherapy. By using the liposomal composition of the present invention, it is possible to reduce the tendency of cancer cells subjected to chemotherapy to develop resistance to the chemotherapeutic agents used for chemotherapy such as anthracycline glycosides. This method includes administering to a host a pharmaceutical composition of a liposomal encapsulated taxane of the present invention in accordance with the administration protocol.

Taxanes and the anti-neoplastic derivatives thereof may be used to treat any form of mammalian cancer. Such compounds are thought to function by promoting the assembly of microtubules or prohibiting the tubulin disassembly process. Taxane and the anti-neoplastic derivatives thereof are of particular advantageous use in the treatment of mammalian lymphoma, ovarian, breast, lung and colon cancer, and particularly those conditions in humans.

The present liposome compositions can be administered intravenously, intraperitoneally, to an isolated portion of a mammalian body particularly a human body, such as an arm or leg, or in the case of a human, a hand, or can be injected directly into a tumor.

The following examples further illustrate the present invention but, of course, should not be construed as in any way limiting its scope.

EXAMPLE 1

Paclitaxel can be encapsulated in liposomes of cardiolipin, phosphatidylcholine, cholesterol and ∝-tocopherol. The composition described in this example, provides for over 90% encapsulation of the drug in liposomes. The paclitaxel in liposomal formulation is stable for days at room temperature and at −20° C. for at least 5 months. No degradation or precipitation of paclitaxel is observed at any storage temperature and the preparation appears to be ideally suited for systemic administration in accordance with the present invention.

The proportion of lipids per mg of paclitaxel is:
1.8 mg cardiolipin
9.0 mg phophatidylcholine
3.0 mg cholesterol
0.1 mg ∝-tocopheryl The liposome encapsulated paclitaxel can be manufactured using the following procedure.

8.89 kilograms of t-butyl alcohol are added to a 12.0 liter flask and heated to 40-45° C. The following additions are made sequentially with mixing until dissolution and heating at 40-45° C.: 3.412 grams of D-α-tocopheryl acid succinate, 205 grams of egg phosphatidylcholine, 22.78 grams of paclitaxel, 41.00 grams of tetramyristoyl cardiolipin, 68.33 grams of cholesterol.

The resulting solution is filtered through a 0.22 micron filter. The resulting filtrate is filled into sterile vials, each containing about 10.1 grams of filtrate. The vials are stoppered and subjected to lyophilization. They can be stored at −20° C. until use.

Liposomes are prepared from the dry lipid film, as needed, with 25 ml of normal saline solution. The mixture is allowed to hydrate at room temperature for about one hour, after which time the vials are vortexed for about one minute and sonicated for about 10 minutes in a bath type sonicator at maximum frequency. An appropriate amount of the contents of the vial can be transferred to an infusion bag and infused into a patient in accordance with the present invention.

EXAMPLE 2

The following study demonstrates that a large quantity of taxane can be rapidly administered to humans without inducing a substantial toxic reaction. Both hematological toxicity and nonhematological toxicity were evaluated. In addition, the study was used to determine in human patients the dose-limiting toxicity, the maximum tolerated dose and the untolerated dose for the liposomal formulation described in Example 1.

Vials containing liposomal paclitaxel were prepared as in Example 1. The preparations were 1 mg/ml paclitaxel in liposomes. The contents of the vials were transferred to infusion bags at the appropriate dosages and administered to patients over about a 45 minute period.

Patients selected for the study had a measurable or evaluable metastatic or locally recurrent malignancy and had no significant hope of cure or palliation by other conventional therapies. In addition, they had no evidence of spinal cord compression or carcinomatous meningitis. Patients had not undergone chemotherapy or radiotherapy within the four weeks prior to treatment. Those patients that had undergone prior chemotherapy or radiotherapy exhibited complete hematologic recovery prior to treatment in this study. All patients had an ECOG (Eastern Cooperative Oncology Group) performance status of 0 or 1 and had a life expectancy of at least 3 months. Patients in the study were all over the age of 18, were free of infection and had recovered from the effects of any major surgery which must have occurred more than three weeks prior to entering the study. Within the immediate two weeks prior to the instant tests all patients had a white blood cell count of over 3000/mm$^3$, a platelet count of over 100,000/mm$^3$, serum creatinine of less than 1.8 mg/dl or creatinine clearance of more than 60/cc/min and serum bilirubin of less than 1.5 mg/dl.

Treatments were administered intravenously over about a 45 minute period. At least three patients were treated at each dosage level. Dosages were about 90 mg/m$^2$, 135 mg/m$^2$, 175 mg/m$^2$, 250 mg/m$^2$, and 300 mg/m$^2$ allowing for normal laboratory and therapeutic dose variation. The formulation was given as a single agent without pretreatment with steroids, antihistamines or other therapeutic agents such as anaphylaxis inhibitors. Where the treating physician considered it appropriate, treatments were repeated every 21 days. Each patient was subjected to a single treatment regimen.

Hematologic toxicity was evaluated in test patients by taking blood specimens of 5 mls from each patient. Samples were taken just prior to drug infusion, at the end of the infusion (time=0), then at 2, 4, 6, 10, 20, 30, 60, 240 minutes and 24 hours after infusion. The samples were collected in heparinized tubes which were gently inverted after filling to ensure mixing of the heparinized blood. The vials were kept cool until the plasma was isolated from each sample. As soon as practical, the samples were centrifuged at 2000 rpm, for 15 minutes to collect the plasma layer. Approximately 1 or 2 ml of the plasma was transferred to a cryotube which was capped and immediately frozen at −20° C. in an upright position until hematological toxicity analysis. Nonhematological toxicity and drug efficacy were also evaluated. The results of this study are shown in Table I below.

Common toxicity grades established by the National Cancer Institute were employed to determine drug toxicity. Dose-limiting toxicity is defined as any grade 3 or higher non-hematologic toxicity for 7 or more days occurring during cycle 1 of chemotherapy. An untolerable dose is defined as the dose level at which at least 1/3 to 2/3 of the patients have dose-limiting toxicity. The maximum tolerated dose level is defined as the dose level at which 0/6 or 1/6 patients experience dose-limiting toxicity and at least 2/3 or 4/6 patients treated at the next higher dose level experience dose-limiting toxicity.

This study demonstrated that a large quantity of taxane could be administered to a human without inducing a substantial hematological or nonhematological toxic reaction. Nonhematological toxicity was generally minor but became more pronounced at the highest dosage level. Similarly, hematological toxicity was mild but became more pronounced at the highest dosage. At least 300 mg/m$^2$ of taxane could be administered to a human patient in a 45 minute period without inducing substantial hematological toxicity or anaphylaxis. The dose limiting toxicity was about 300 mg/m$^2$ when drug was administered in a 45 minute period. The untolerable and maximum tolerable doses were not determinable from this study but were at least 300 mg/m$^2$. With one exception, the cancer had not progressed or was improved in each of the patients studied.

TABLE I

| Patient Number | Treatment Cycles | Dose (mg/m²) | Heme Toxicity[1] | Nonhematological Toxicity | Best Response | Off study due to |
|---|---|---|---|---|---|---|
| 001 | 2 | 90 | None | HSR[2] | | P.D.[3] |
| 002 | 11+ | 90 | Mild | | Stable | |
| 003 | 6 | 90 | Mild | (Seizure) | Stable | P.D. |
| 004 | 2 | 135 | | HSR | | P.D. |
| 005 | 6 | 135 | Mild | Muscular & hepatic | Stable | elective |
| 006 | 8+ | 135 | Mild | (HA, fever, pharyngitis, wheezing) | Progressed | |
| 007 | 3 | 175 | Mild | (diarrhea) | | P.D. |
| 008 | 2 | 175 | Mild | Mild hepatic | | P.D. |
| 009 | 1 | 175 | Mild | Recurrent HSR; Nausea/fatigue; Mild hepatic | | HSR |
| 010 | 2 | 250 | Mod | (hemoptysis) | | P.D. |
| 011 | 4+ | 250 | Mild | Mild hepatic (HA, diarrhea, chills & sweats) Esophagitis grade 3 after cycle 3 | Stable | |
| 012 | 3 | 250 | Mild | Mild hepatic | | P.D. |
| 013 | 2+ | 250 | Mild | Mild GI, HSR | | |
| 014 | 2+ | 300 | Mod | Hepatic, Esophagitis grade 3 | Improved | |
| 015 | 1+ | 300 | Severe | Mild HSR, Hepatic | | |
| 016 | 1+ | 300 | Severe | Esophagitis grade 3 | | |

[1]neutropenia, anemia, thrombopenia
[2]hypersensitivity reaction: flushing, back pain, pruritis
[3]physician or patient discretion All of the references cited herein, including patents, patent applications, and publications, are hereby incorporated in their entireties by reference.

While this invention has been described with an emphasis upon preferred embodiments, it will be obvious to those of ordinary skill in the art that variations of the preferred embodiments may be used and that it is intended that the invention may be practiced otherwise than as specifically described herein. Accordingly, this invention includes all modifications encompassed within the spirit and scope of the invention as defined by the following claims.

I claim:

1. A method of administering a taxane to a human patient in need of treatment with a taxane comprising administering a pharmaceutical composition to said human patient over a period between about 45 minutes to about one hour in an amount from about 135 mg/m² to about 300 mg/m² wherein said pharmaceutical composition is a liposomal encapsulated taxane.

2. The method of claim 1, wherein said taxane is selected from the group consisting of paclitaxel, 7-epipaclitaxel, t-acetyl paclitaxel, 10-desacetyl-paclitaxel, 10-desacetyl-7-epipaclitaxel, 7-xylosylpaclitaxel, 10-desacetyl-7-glutarylpaclitaxel, 7-N,N-dimethylglycylpaclitaxel, 7-L-alanylpaclitaxel, taxotere, and mixtures thereof.

3. The method of claim 1, wherein said pharmaceutical composition further comprises a pharmaceutically acceptable excipient.

4. The method of claim 1, wherein said pharmaceutical composition further comprises cardiolipin.

5. The method of claim 4, wherein said cardiolipin is selected from the group consisting of natural cardiolipin and synthetic cardiolipin.

6. The method of claim 1, wherein said amount of said taxane is about 135 mg/m².

7. The method of claim 1, wherein said amount of said taxane is about 175 mg/m².

8. The method of claim 1, wherein said amount of said taxane is about 250 mg/m².

9. The method of claim 1, wherein said amount of said taxane is about 300 mg/m².

10. The method of claim 1, wherein said patient is suffering from ovarian cancer, breast cancer, lung cancer, lymphoma or colon cancer.

11. The method of claim 1, wherein said liposomal encapsulated taxane is administered by intravenous infusion.

12. The method of claim 1, wherein said administration of said liposomal encapsulated taxane is repeated at least once every 21 days.

13. The method of claim 1, wherein said administration of said liposome encapsulated taxane is administered intraperitoneally to patients suffering from cancer.

14. The method of claim 13, wherein said administration of said liposome encapsulated taxane is administered intraperitoneally to patients suffering from colon cancer.

15. A method of treating a human having cancer with a taxane comprising administering a large quantity of a liposomal taxane to said human between about 45 minutes to about one hour without inducing a substantial toxic reaction.

16. The method of claim 15 in which the liposomal taxane is administered intravenously.

17. The method of claim 15 in which the liposomal taxane is administered as a single agent without pretreatment by steroids, antihistamines, H₂-antagonists or antihypersensitivity agents.

18. The method of claim 15 in which substantial nonhematological toxicity is not induced.

19. The method of claim 15 in which substantial anaphylaxis is not induced.

20. The method of claim 15 in which the large quantity of the liposomal taxane ranges from about 135 mg/m² to 300 mg/m².

21. The method of claim 15 in which the large quantity of the liposomal taxane ranges from about 175 mg/m$^2$ to 300 mg/m$^2$.

22. The method of claim 15 in which the large quantity of the liposomal taxane ranges from about 175 mg/m$^2$ to 250 mg/m$^2$.

23. The method of claim 15 in which the large quantity of the liposomal taxane is about 250 mg/m$^2$.

24. The method of claim 15, in which the liposomal taxane is rapidly administered between about 45 minutes and about one hour.

25. The method of claim 15, in which the liposomal taxane is rapidly administered in about 45 minutes.

26. The method of claim 15 further comprising repeating the step of administering a large quantity of a liposomal taxane to a human between about 45 minutes to about one hour without inducing a substantial toxic reaction.

27. The method of claim 26 wherein the repeating step occurs in 21 days.

28. A method of administering a taxane to a human patient in need of treatment with taxane comprising administering a pharmaceutical composition to said human patient in an amount of at least about 300 mg/m$^2$ over a period of between about 45 minutes to about one hour wherein said pharmaceutical composition is a liposomal encapsulated taxane.

29. A method of treating a human with a taxane comprising administering a liposomal taxane ranging from about 75 mg/m$^2$ to about 300 mg/m$^2$ to a human between about 45 minutes to about one hour without inducing a substantial toxic reaction.

30. The method of claim 29 in which the liposomal taxane is administered intravenously.

31. The method of claim 29 in which the liposomal taxane is administered as a single agent without pretreatment by steroids, antihistamines, H$_2$-antagonists or antihypersensitivity agents.

32. The method of claim 29 in which substantial nonhematological toxicity is not induced.

33. The method of claim 29 in which substantial anaphylaxis is not induced.

34. The method of claim 29 in which the large quantity of the liposomal taxane ranges from about 90 to 300 mg/m$^2$.

35. The method of claim 29 in which the large quantity of the liposomal taxane ranges from about 135 to 300 mg/m$^2$.

36. The method of claim 29 in which the large quantity of the liposomal taxane ranges from about 175 to 300 mg/m$^2$.

37. The method of claim 29 in which the large quantity of the liposomal taxane ranges from 175 to 300 mg/m$^2$.

38. The method of claim 29 in which the large quantity of the liposomal taxane is about 250 mg/m$^2$.

39. The method of claim 29, in which the liposomal taxane is rapidly administered in about 45 minutes to about one hour.

40. The method of claim 29, in which the liposomal taxane is rapidly administered in about 45 minutes.

41. The method of claim 29, further comprising repeating the step of administering a liposomal taxane ranging from about 75 mg/m$^2$ to about 300 mg/m$^2$ to a human between about 45 minutes to about one hour without inducing substantial hematological or nonhematological toxicity.

42. The method of claim 41, wherein the repeating step occurs in 21 days.

* * * * *